(12) United States Patent
Vogt (10) Patent No.: US 9,622,866 B2
(45) Date of Patent: Apr. 18, 2017

(54) TWO-COMPONENT KNEE SPACER WITH RECESSES

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 0 days.

(21) Appl. No.: 14/190,819

(22) Filed: Feb. 26, 2014

(65) Prior Publication Data

US 2014/0288659 A1 Sep. 25, 2014

(30) Foreign Application Priority Data

Mar. 22, 2013 (DE) ........................ 10 2013 205 156

(51) Int. Cl.
*A61F 2/38* (2006.01)
*A61F 2/30* (2006.01)
*A61F 2/46* (2006.01)

(52) U.S. Cl.
CPC ................ *A61F 2/385* (2013.01); *A61F 2/38* (2013.01); *A61F 2/389* (2013.01); *A61F 2/3859* (2013.01);
(Continued)

(58) Field of Classification Search
CPC ............................... A61F 2/389; A61F 2/3859
See application file for complete search history.

(56) References Cited

U.S. PATENT DOCUMENTS

| 5,123,927 A | 6/1992 | Duncan et al. |
| 5,330,532 A | 7/1994 | Ranawat |

(Continued)

FOREIGN PATENT DOCUMENTS

| CN | 1216585 C | 9/2003 |
| CN | 102917670 A | 2/2013 |

(Continued)

OTHER PUBLICATIONS

Australian Office Action for corresponding Australian Application No. 2014201724 dated Jan. 7, 2015.
(Continued)

*Primary Examiner* — Katrina Stransky
*Assistant Examiner* — Daniel Bissing
(74) *Attorney, Agent, or Firm* — Norris McLaughlin & Marcus, P.A.

(57) ABSTRACT

The invention relates to a knee spacer for temporary replacement of an artificial knee joint, whereby the knee spacer comprises a tibial component and a femoral component as separate components, which can be moved with respect to each other when inserted in a patient, and whereby the tibial component and the femoral component each comprise at least one running surface by means of which the tibial component and the femoral component can be placed against each other such as to be mobile in their patient-inserted state, and the tibial component comprises an anchoring surface that is arranged opposite to the running surface side and is provided for connecting the tibial component to the tibia by means of a bone cement, and the femoral component to comprise an anchoring surface that is arranged opposite to the running surface side and is provided for connecting the femoral component to the femur, whereby the tibial component and the femoral component each comprise at least two recesses that extend from the anchoring surface towards the running surface side into the running surface side, whereby the openings of the recesses are arranged appropriately in the running surface side of the components such that they do not slide over the running surface of the respective other component during articulation of the knee spacer.

The invention also relates to a method for the manufacture of a knee spacer, in which the tibial component and the
(Continued)

femoral component are produced as separate components and in which at least two recesses are formed in the tibial component and at least two recesses are formed in the femoral component, as well as to the use of said knee spacer as temporary spacer in a knee of a patient.

14 Claims, 5 Drawing Sheets

(52) U.S. Cl.
CPC ........... *A61F 2002/30224* (2013.01); *A61F 2002/30672* (2013.01); *A61F 2002/30677* (2013.01); *A61F 2002/30878* (2013.01); *A61F 2002/4631* (2013.01); *A61F 2240/001* (2013.01); *A61F 2310/00353* (2013.01); *Y10T 29/49* (2015.01)

(56) References Cited

U.S. PATENT DOCUMENTS

| | | | |
|---|---|---|---|
| 5,702,458 | A | 12/1997 | Burstein et al. |
| 2004/0054417 | A1 | 3/2004 | Soffiati et al. |
| 2005/0085918 | A1 | 4/2005 | Soffiati et al. |
| 2007/0173946 | A1 | 7/2007 | Bonutti |
| 2007/0222114 | A1* | 9/2007 | Ziran .............. A61F 2/30942 264/279 |
| 2012/0310362 | A1* | 12/2012 | Li .................. A61F 2/38 623/20.32 |
| 2012/0323334 | A1 | 12/2012 | Jones et al. |
| 2013/0073049 | A1 | 3/2013 | Faccioli et al. |
| 2013/0150966 | A1* | 6/2013 | Westenberg ........ 623/16.11 |
| 2015/0088264 | A1 | 3/2015 | Li et al. |

FOREIGN PATENT DOCUMENTS

| | | | | |
|---|---|---|---|---|
| EP | 1274374 | B1 | 12/2008 | |
| JP | 2003529440 | A | 10/2003 | |
| JP | 2010088921 | A | 4/2010 | |
| WO | WO2014074095 | A1 * | 11/2012 | |
| WO | 2012/173740 | A1 | 12/2012 | |
| WO | WO 2014074095 | A1 * | 5/2014 | ............. A61F 2/38 |

OTHER PUBLICATIONS

Japanese Office Action for corresponding Japanese Application No. 2014-033195 dated Apr. 7, 2015.
Hovelius et al, "An alternative method for exchange operation of infected arthroplasty", Acta Orthop. Scand. 50: 93-96 (1979).
Younger et al, "The outcome of two-stage arthroplasty using a custom-made interval spacer to treat the infected hip", J. Arthroplasty 12: 615-623 (1997).
Jones et al, "Salvage of failed total knee arthroplasty: the 'beef-burger' procedure", J. Bone Joint Sum. Br, 71: 856-857 (1989).
Cohen et al, "Two-stage reimplantation of septic total knee arthroplasty, Report of three cases using an antibiotic-PMMA spacer block", J. Arthroplasty 3: 369-377 (1988).
McPherson et al, "Techniques in arthroplasty. Use of an articulated PMMA spacer in the infected total knee arthroplasty", J. Arthroplasty 10: 87-89 (1995).
German Office Action for corresponding German Application No. 10 2013 205 156.5 dated Nov. 13, 2013.
Chinese Office Action for corresponding Chinese Application No. 201410107197.9 dated May 18, 2016.

* cited by examiner

TWO-COMPONENT KNEE SPACER WITH RECESSES

The invention relates to a knee spacer for temporary replacement of an artificial knee joint, whereby the knee spacer comprises a tibial component and a femoral component as separate components that are mobile with respect to each other in their patient-inserted state. The invention also relates to a method for the manufacture of a knee spacer and the use of said knee spacer.

Accordingly, the subject matter of the invention is a two-component knee spacer and/or a two-component knee spacer system for use as temporary spacer in the scope of two-stage septic revision surgeries of knee endoprostheses.

Articular endoprostheses currently have a service life of several years, for example on average more than ten and up to fifteen years in the case of cemented hip endoprostheses. However, undesirable loosening of the articular endoprostheses can occur before the end of the usual service life. This can concern either septic or aseptic loosening. Aseptic loosening means that no microbial germs are detectable yet. There are many causes of aseptic loosening. Aseptic loosening is often related to abrasion at the sliding surfaces of articular endoprostheses.

The loosening process in septic loosening is induced by microbial germs. This can either be early or late infections depending on the time of manifestation. Septic loosening is a very serious disease for the patient and its treatment is very expensive. It is customary to perform a revision surgery in cases of aseptic and septic loosening alike. This can proceed as a one-stage or a two-stage revision surgery. Two-stage revision surgeries are very common in cases of septic loosening.

In a two-stage revision surgery, the infected articular endoprosthesis is removed in a first surgery (OP) followed by debridement (removal of the infected tissue) and subsequent insertion of a temporary place-holder, a so-called spacer. Said spacer occupies the space previously occupied by the revised endoprosthesis until the manifest infection has subsided. Said place-holder function is very important in order to effectively prevent muscular atrophy during this period of time and in order to stabilise the existing resection scenario.

There are non-articulated and articulated spacers available. Articulated spacers replicate the function of the joint and allow the afflixted limbs to have a certain degree of mobility. This allows the patient to be mobilised early. Therefore, the insertion of articulated spacers is very popular to date. The spacer is removed in a second surgery, another debridement is done before implanting a cemented or cement-free revision articular endoprosthesis.

The use of spacers is originally based on the work of Hovelius and Josefsson (Hovelius L, Josefsson G (1979), "An alternative method for exchange operation of infected arthroplasty", Acta Orthop. Scand. 50: 93-96). Other early work on spacers includes Younger (Younger A S, Duncan C P, Masri B A, McGraw R W (1997), "The outcome of two-stage arthroplasty using a custom-made interval spacer to treat the infected hip", J. Arthroplasty 12: 615-623), Jones (Jones W A, Wroblewski B M (1989), "Salvage of failed total knee arthroplasty: the 'beefburger' procedure", J. Bone Joint Surg. Br. 71: 856-857), and Cohen (Cohen J C, Hozack W J, Cuckler J M, Booth R E Jr (1988), "Two-stage reimplantation of septic total knee arthroplasty, Report of three cases using an antibiotic-PMMA spacer block", J. Arthroplasty 3: 369-377). McPherson described a concept according to which spacers can be manufactured from bone cement exclusively (McPherson E J, Lewonowski K, Dorr L D (1995), "Techniques in arthroplasty. Use of an articulated PMMA spacer in the infected total knee arthroplasty", J. Arthroplasty 10: 87-89).

Spacers equipped with antibiotics for temporary replacement of knee, hip, and shoulder endoprostheses are available on the market. Knee spacers generally consist of two components, i.e. a tibial component and a femoral component. A spacer or spacer system typical of this type is disclosed in EP 1 274 374 A1. Referring to knee spacers, both the tibial component and the femoral component need to be anchored, in additional, to the proximal tibia and the distal femur using polymethylmethacrylate bone cement. In this context, the polymethylmethacrylate bone cement adheres to the surface of the spacer components. The surface of the spacer components, which usually consist of cured, antibiotics-doped polymethylmethacrylate bone cement, is dissolved to a certain degree by the methylmethacrylate of the polymethylmethacrylate bone cement. This leads to a bond being established to the curing polymethylmethacrylate bone cement. This is the main foundation of the adhesion of the polymethylmethacrylate bone cement to the surface of the spacer components. One difficulty, though, is that torsional forces resulting from the walking motions of patients during the period of implantation, which can be any time from two weeks up to six months depending on the design of treatment, may cause the spacer components to detach from the polymethylmethacrylate bone cement used for anchoring.

Accordingly, it is the object of the invention to overcome the disadvantages of the prior art. Specifically, the invention is to provide a stable articulated knee spacer that can be used to produce robust connections to femur and tibia. The spacer is to be particularly mobile and to remain stable even when exposed to frequent motions. Concurrently, the spacer is to be inexpensive to manufacture.

The objects of the invention are met by a knee spacer for temporary replacement of an artificial knee joint, whereby the knee spacer comprises a tibial component and a femoral component as separate components, which can be moved with respect to each other in their patient-inserted state, and whereby the tibial component and the femoral component each comprise at least one running surface by means of which the tibial component and the femoral component can be placed against each other such as to be mobile for their patient-inserted state, and whereby the tibial component comprises an anchoring surface that is arranged to be situated opposite to the running surface side and is provided for connecting the tibial component to the tibia by means of a bone cement, and whereby the femoral component comprises an anchoring surface that is arranged to be situated opposite to the running surface side and is provided for connecting the femoral component to the femur, whereby the tibial component and the femoral component each comprise at least two recesses that extend from the anchoring surface towards the running surface side into the running surface side, whereby the openings of the recesses are arranged appropriately in the running surface side of the components such that they do not slide over the running surface of the respective other component during articulation of the knee spacer.

The patient-inserted state shall be defined to be the arrangement, in which the components of the knee spacer are to be or are cemented in the knee of the patient in order to form a functional, i.e. mobile, temporary implant.

Due to the length of the recesses up to the running surface side, extensions of the bone cement that are particularly long-extended and are thus stable after curing and hold the components can be formed.

Preventing the components from sliding over the openings of the recesses on the running surface side during articulation of the knee spacer, i.e. during an intended rotation of the components that are inserted in the patient and touch against each other, allows parts of the bone cement, which is used for fixation of the components and has recesses extend through it into the openings on the running surface side, to be prevented from being abraded by the components sliding over it. It can thus be prevented that parts of the abraded material adversely affect the knee region and/or deteriorate the articulation of the knee spacer.

Knee spacers according to the invention can provide the recesses in the tibial component and femoral component to be arranged on the periphery thereof.

Having the recesses arranged at the periphery produces particularly robust connections of the components to the bone cement affixing the components to the bone due to the long levers up to the recesses. Moreover, the torques and forces associated with walking can be received particularly well through the long levers.

The invention can preferably provide just as well that at least two of the recesses are arranged opposite from each other in appropriate manner such that, in the patient-inserted state of the components, bone cement extensions formed in the recesses clamp the components in appropriate manner such that regions of the components, preferably central regions of the components, are arranged between the extensions.

This arrangement allows for further stabilisation of the connection of the components to the bone cement to be attained. In this context, clamping means that opposite forces can act by means of the internal walls of two recesses. In this context, the forces preferably act through-going on the inside of the components. These forces attain particularly stable fixation of the components and variable reception of the forces associated with walking. The extensions are formed by the bone cement affixing the components to the bone. The bone cement extensions thus form a U-shaped insertion in two recesses each.

Moreover, the invention can provide the recesses not to extend into the running surface.

This prevents abrasion of parts of the bone cement that might extend to the running surface during articulation of the knee spacer.

A refinement of the invention proposes projections for anchoring the bone cement to be arranged in the recesses.

Due to said projections, around which the bone cement can flow for fixation of the components to the tibia and/or femur, we attained particularly stable anchoring of the components to the bone.

A particularly preferred refinement of the invention provides the tibial component and/or the femoral component, in the inserted state, to be asymmetrical to a plane parallel to the sagittal plane of the patient, preferably to be asymmetrical by means of the arrangement and/or shape of a recess for receiving the cruciate ligament of the patient and/or to be asymmetrical by means of the arrangement and/or shape of the recesses.

Breaking the symmetry of the knee spacer allows anatomy-based asymmetries of the walking motion and associated torsional forces to be taken into account. However, the recesses can instead be symmetrical to the plane, which, in the inserted state, is parallel to the sagittal plane of the patient. However, for receiving the non-symmetrical torsional forces acting on the inserted spacer during walking, it is preferred that the recesses, by means of which the torsional forces are to be transmitted to the cured bone cement, are not symmetrical to the plane, which, in the inserted state, is parallel to the sagittal plane of the patient.

Moreover, the invention can provide recesses to be designed as cylinders, truncated cones and/or multi-sided prisms, whereby at least one front side of the cylinders, truncated cones and/or prisms is open towards the anchoring surface, in particular both front faces of the cylinders, truncated cones and/or prisms are open to the anchoring surface and to the running surface side, and whereby the jacket surfaces of the cylinders, truncated cones and/or prisms are preferably closed in longitudinal direction or are punctured once in axial direction.

Said symmetries are well-suited for receiving the forces during walking and they are easy to manufacture. According to the invention, the symmetry of the recesses can be broken by means of projections for anchoring the bone cement, if applicable.

The invention also proposes that at least one first guide element is arranged on the running surface side of the tibial component and at least one second guide element is arranged on the running surface side of the femoral component, whereby the guide elements, in the patient-inserted state, prevent the femoral component from shifting with respect to the tibial component in the direction of a plane parallel to the sagittal plane by means of a form-fit being established upon a rotary motion of the two components with respect to each other.

The guide elements ensure safe rotation of the component with respect to each other about just one axis such that the knee formed with the knee spacer is prevented from undesired twisting.

For implementation of knee spacers according to the invention, the invention can provide the tibial component and the femoral component to be made up from at least one plastic material and/or metal, preferably to consist of plastic material and/or metal, particularly preferably of polymethylmethacrylate, and even more particularly preferably of antibiotics-doped cured polymethylmethacrylate bone cement.

Said materials are particularly well-suited for the manufacture of knee spacers according to the invention.

The invention can also provide the tibial component to comprise a stem that extends from a central position of the anchoring surface at an angle of between 85° and 90° away from the anchoring surface, preferably extends perpendicularly away from the anchoring surface, and the stem to be provided for anchoring in a recess in the tibia, whereby the stem extending away from the anchoring surface preferably is convergent, at least over regions thereof.

The stem serves for anchoring in the tibia. This allows a particularly stable connection to the tibia to be attained.

The invention can just as well provide multiple spacers to be arranged on the anchoring surface of at least one of the components, preferably of both components, whereby the spacers extending away from the anchoring surface preferably are convergent, at least over regions thereof, and whereby the stem particularly preferably is at least four times as high as the spacers of the anchoring surface of the tibial component.

The purpose of the spacers is to have a sufficient amount and a sufficiently thick layer of bone cement for connecting the two components to the bone to remain and to thus generate a stable connection of the components to the bones.

The objects of the invention are also met by a method for the manufacture of a knee spacer, in which the tibial component and the femoral component are produced as separate components and in which at least two recesses are formed in the tibial component and at least two recesses are formed in the femoral component.

The effect of the recesses is stabilisation of the structure of the knee including the knee spacer during walking motions of the patient.

And lastly, the objects of the invention are also met through the use of a knee spacer of this type as temporary spacer in a knee of a patient.

The invention is based on the surprising finding that having recesses in the two components of the knee spacers allows the bone cement to cure in said recesses and to thus generate a mechanically stable connection between the components of the knee spacer and the connecting bone cement that is capable of receiving the torsional forces occurring during walking without the bone cement detaching from the components of the knee spacer.

Accordingly, the invention provides a two-component knee spacer that allows undesired torsion of the tibial component and also of the femoral component with respect to the polymethylmethacrylate bone cement used for temporary anchoring to be largely excluded for the time the spacer is implanted. The torsional forces are received well and over large surface areas by the bone cement extensions produced in the recesses such that force or torque peaks, which might destroy the connection or fracture the bone cement, do not arise at any site of the connection between the knee spacer or the knee spacer components and the bone cement.

The underlying rationale of the invention is that the tibial component and the femoral component each possess at least two recesses connecting the distal and the proximal surfaces of the respective components such that the polymethylmethacrylate bone cement used for fixation can engage the recesses leading such that a form-fit of the polymethylmethacrylate bone cement and the tibial component and a form-fit of the polymethylmethacrylate bone cement and the femoral component is established. Due to at least two recesses being arranged in each component, torsion of the tibial component and femoral component with respect to the polymethylmethacrylate bone cement used for temporary anchoring is safely excluded. It is also essential in this context that the recesses are not situated inside the running surfaces or sliding surfaces of the tibial component and femoral component. It is also essential to the invention that the tibial component is suitably arranged with respect to the femoral component such that the running pair and/or sliding pair made up by the at least one proximal running surface of the tibial component and the at least one distal running surface of the femoral component does not extend across recesses of the tibial component and femoral component.

The knee spacer according to the invention is used as temporary spacer in the scope of two-stage septic revision surgeries of knee endoprostheses.

Exemplary embodiments of the invention shall be illustrated in the following on the basis of five schematic figures, though without limiting the scope of the invention. In the figures.

Figure 1:
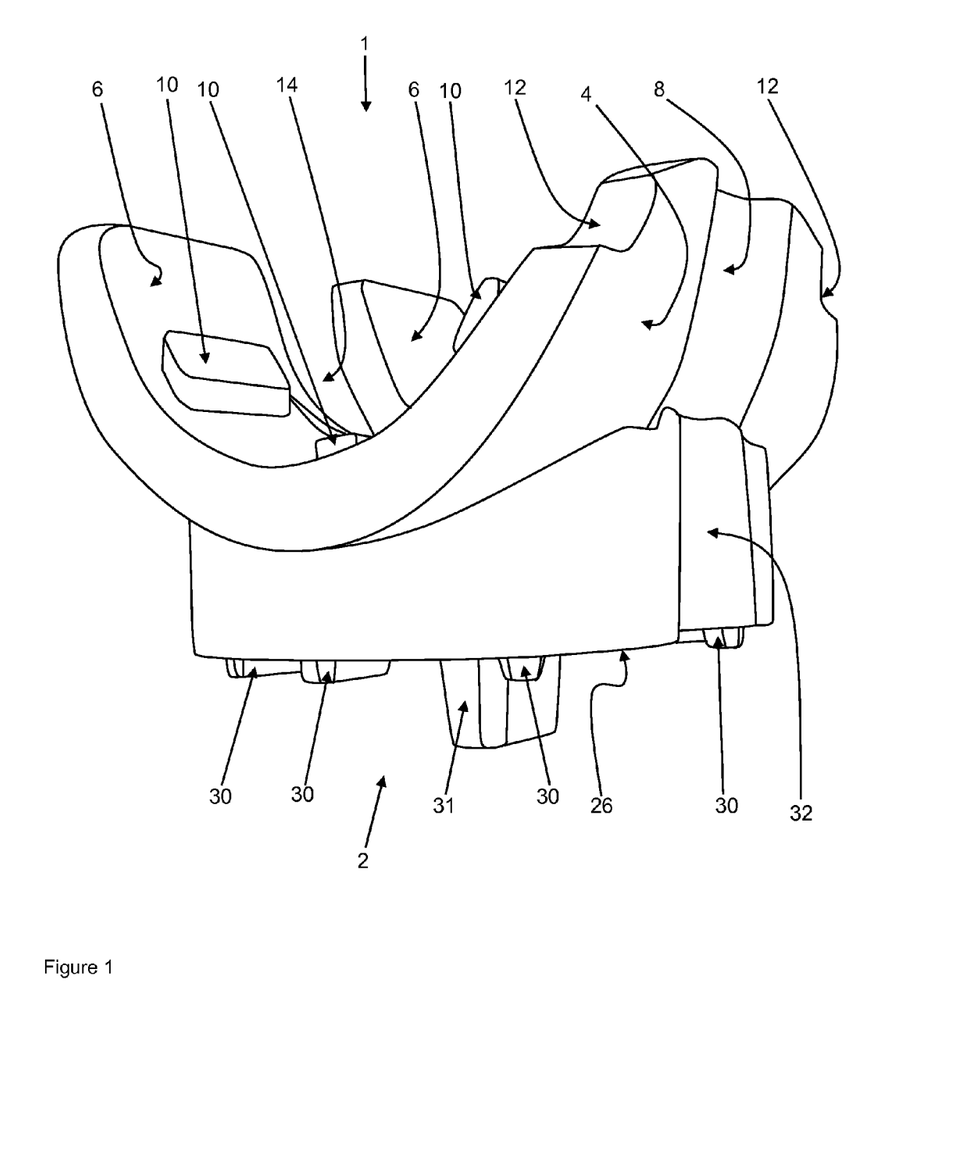
FIG. 1: shows a schematic perspective view of a knee spacer according to the invention.
Figure 2:
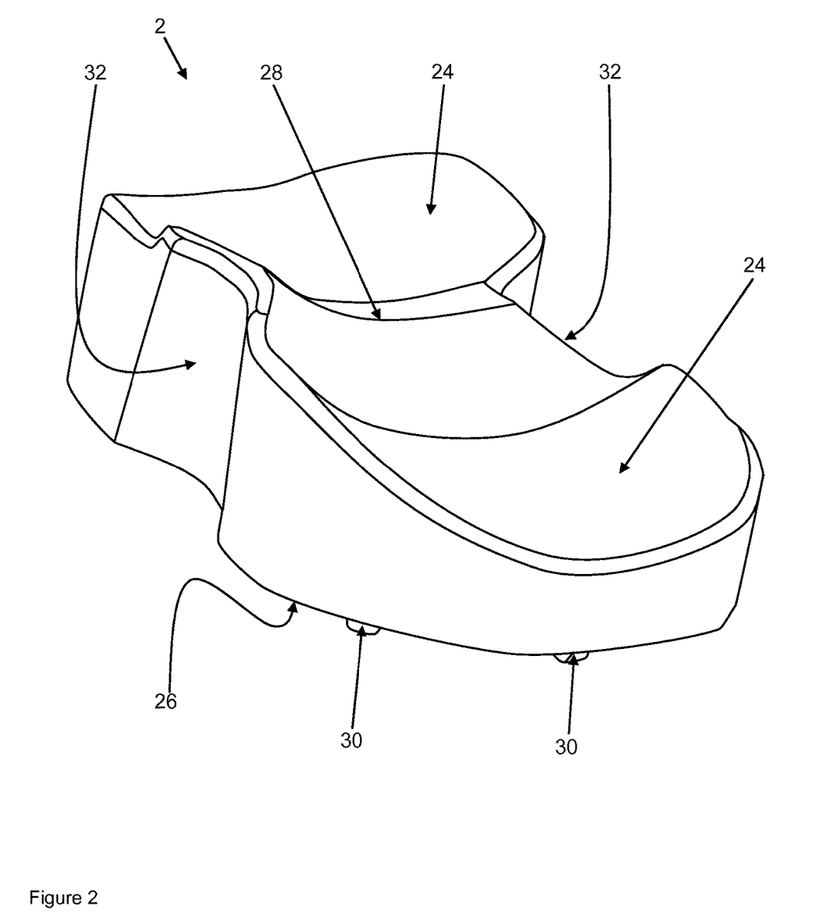
FIG. 2: shows a schematic perspective view of the tibial component of the knee spacer according to the invention.
Figure 3:
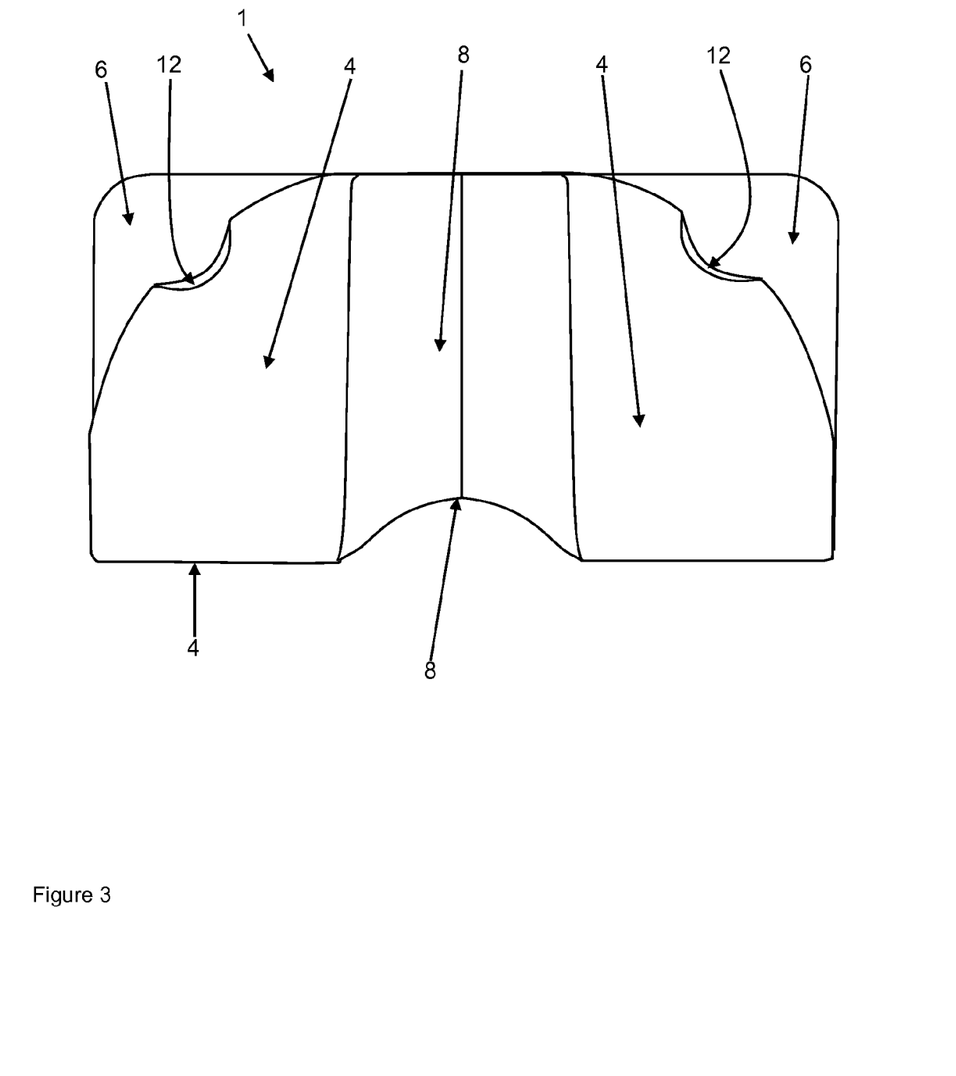
FIG. 3: shows a schematic side view of the femoral component of the knee spacer according to the invention.
Figure 4:
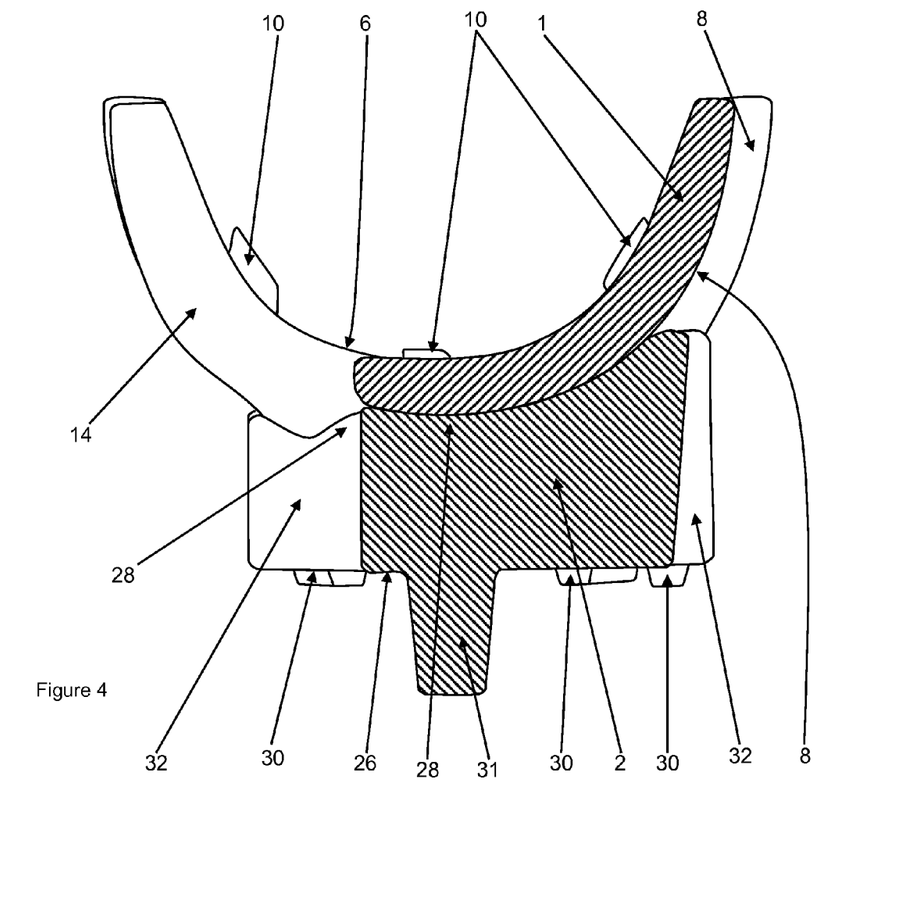
FIG. 4: shows a schematic cross-sectional view of the knee spacer according to the invention.

FIG. 1 shows a schematic perspective view of a knee spacer according to the invention. The knee spacer comprises a femoral component 1 (on the top in FIG. 1) and a tibial component 2 (on the bottom in FIG. 1). FIG. 2 shows a schematic perspective view of the tibial component 2 of the knee spacer according to the invention according to FIG. 1, and FIG. 3 shows a schematic side view of the femoral component 1 of the knee spacer according to the invention according to FIG. 1, each individually and separately. Moreover, FIG. 4 shows a schematic cross-sectional view of the knee spacer according to the invention according to FIG. 1, whereby the bisected surfaces are shown cross-hatched.

The femoral component 1 comprises an underside that is curved outwards, as running surface 4. Accordingly, the side opposite to the running surface 4 is curved inwards and forms an anchoring surface 6 for fixation of the femoral component 1 to a femur (thigh bone—not shown). Moreover, a depression 8 is provided as guide element on the running surface side of femoral component 1 (pointing downwards in FIGS. 1, 3, and 4). The running surface 4 is cylinder-shaped. The running surface 4 and the depression form a joint jacket segment of a body of rotation such that the running surface side can be rotated and can slide on a matching rotationally symmetrical internal curvature. Alternatively, but less preferred, the running surface side can roll on a planar or less strongly curved internal curvature.

Six spacers 10 are provided on the anchoring surface 6 and are used to ensure that a minimal amount and a minimal thickness of bone cement is present between the femoral component 1 and the femur when the knee spacer is inserted in a patient. The spacers 10 extend parallel to each other away from the anchoring surface 6. The direction into which the spacers 10 extend away from the anchoring surface 6 corresponds to the position of the femur when the femoral component 1 is properly inserted in the patient. The spacers 10 have rectangular base surfaces with rounded corners. The two spacers 10 in the middle form straight general cylinders with rounded rectangular base surfaces, whereas the four other spacers 10 are skewed general cylinders with rounded rectangular base surfaces.

One end of the femoral component 1 has two recesses 12 extend from the anchoring surface 6 to the running surface side opposite from it. The recesses 12 take the geometry of a cylinder jacket segment. The cylinder jacket segment of the recesses 12 comprises approx. 45° of a complete cylinder jacket. The cylinder jacket segments of the recesses 12 each comprise one region that is parallel to each other and between which an external part of the femoral component 1 are arranged.

When the femoral component 1 is cemented to the femur, the extensions of the cured bone cement (not shown) extend into the recesses 12. Said extensions clamp the external region of the femoral component 1 and thus provide for a stable fixation of the femoral component 1 to the femur that is capable of receiving the forces, torsions, and torques occurring during walking without the connection of the femoral component 1 to the femur getting damaged in the process.

The side of the femoral component 1 situated opposite to the two recesses 12 has a broad slit-shaped recess 14 provided on it that is used not only for anchoring like the other recesses 12, but also concurrently for receiving the cruciate ligaments of the patient. The recess 14 and the recesses 12 are situated opposite from each other in appropriate manner such that a stable fixation by means of the bone cement extensions is effected and such that the central regions of the femoral component 1 are also being clamped.

The tibial component 2 (bottom) comprises on its upper side (on the top in FIGS. 1, 2, and 4) a running surface 24 that has the same curvature, but as an internal curvature, as the running surface 4 of the femoral component 1. The running surfaces 4, 24 thus fit into each other in a form-fit.

The underside of the tibial component 2 is designed as a flat and forms the anchoring surface 26 of the tibial component 2 that can be used to affix the tibial component 2 to the tibia (shin bone—not shown). As a matching counterpart to the depression 8 of the femoral component 1, the upper side of the tibial component 2 comprises an elevation 28 as a guide element. The running surface 24 and the elevation 28 form a joint jacket segment 24, 28 of a body of rotation that fits into the jacket segment 4, 8 of a body of rotation of the femoral component 1. For this purpose, the depression 8 and the elevation 28 extend along the circumference of the jacket segments of a body of rotation. These can slide one in the other when the femoral component 1 and the tibial component 2 are patient-inserted and thus are positioned against each other as shown in FIGS. 1 and 4. However, due to the guide elements 8, 28, rotation is possible only about one axis such that the knee spacer replicates a knee joint.

The anchoring surface 26 of the tibial component 2 has eight spacers 30 arranged on it that project away downwards and also serve to ensure that a minimal amount and a minimal thickness of bone cement is arranged between the tibia and the tibial component 2 when the tibial component 2 is inserted in the patient. The spacers 30 are shaped to be slightly conically converging in downward direction. A stem 31, which also extends perpendicularly downwards away from the anchoring surface 26 and also converges slightly conical downwards is provided in the middle of the anchoring surface 26 of the tibial component 2. The stem 31 is to be inserted into a corresponding cavity in the tibia and serves for stabilisation of the knee spacer.

Both the stem 31 and the spacers 30 are truncated cones with rounded rectangular base surfaces and rounded edges.

Two sides of the tibial component 2 have, on the periphery, two recesses 32 situated on them that serve the same purpose as the recesses 12, 14 of the femoral component 1 (see above). Pointing towards the right and backwards in FIG. 2, the recess 32 forms a cylinder jacket segment of approximately half the circumference (i.e.) 180° and, like the recess 14, additionally serves for receiving the cruciate ligament when the knee spacer is patient-inserted. Oriented to the front left in FIG. 2 and also shown in FIG. 1, the recess 32 extends upward conically convergent in the direction of the femoral component 1 and thus forms a truncated cone jacket surface segment.

The recess 32 of the tibial component 2 forming the truncated cone jacket surface segment and two of the spacers 30 are not symmetrical to the middle ridge of the elevation 28 and/or to a plane of the knee spacer that is parallel to the sagittal plane in order to be able to appropriately dissipate the forces and torques occurring during walking such as to match the walking motion. Accordingly, the elevation 28 is situated only approximately between the recesses 32 of the tibial component 2.

The femoral component 1 and the tibial component 2 are present as separate components and are manufactured from a suitable plastic material. Preferably, the two components 1, 2 are manufactured from an antibiotics-doped, cured polymethylmethacrylate bone cement. The same bone cement is used for insertion of the components 1, 2 in the patient and for affixing them to the tibia and femur, respectively.

Figure 5:
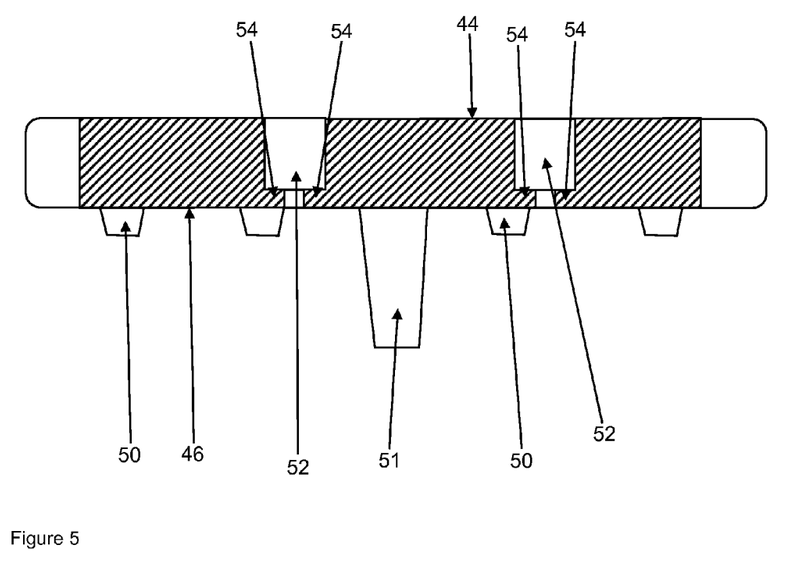
FIG. 5: shows a schematic cross-sectional view of an alternative tibial component of a knee spacer according to the invention.

FIG. 5 shows a schematic cross-sectional view of an alternative tibial component of a knee spacer according to the invention. The tibial component shown has a planar running surface 44 as upper side (on the top in FIG. 5) and, parallel to it, a planar anchoring surface 46 as underside (on the bottom in FIG. 5).

Multiple spacers 50 are provided on the anchoring surface 46 and are to serve the same purpose as the spacers 10, 30 according to FIGS. 1 to 4. Moreover, a stem 51 is also provided at a central position of the anchoring surface 46 of the tibial component and serves the same purpose as the stem 31 of the tibial component 2 according to FIGS. 1 and 2.

Moreover, the tibial component comprises, in the region shown as a section, two recesses 52 that serve the same purpose as the recesses 32 of the tibial component 2 according to FIGS. 1, 2, and 4. Projections 54 are provided in the recesses around and, starting at the anchoring surface 46, can have bone cement flow around them and thus lead to even more stable anchoring of the tibial component on the tibia. Said principle can easily be transferred to the recesses of a femoral component.

Knee spacers preferably have rounded corners and edges rather than sharp edges and corners.

The features of the invention disclosed in the preceding description and in the claims, figures, and exemplary embodiments, can be essential for the implementation of the various embodiments of the invention both alone and in any combination.

LIST OF REFERENCE NUMBERS

1 Femoral component
2 Tibial component
4 Running surface
6 Anchoring surface
8 Depression
10 Spacer
12 Recess
14 Recess
24 Running surface
26 Anchoring surface
28 Elevation
30 Spacer
31 Stem
32 Recess
44 Running surface
46 Anchoring surface
50 Spacer
51 Stem
52 Recess
54 Projection

The invention claimed is:

1. A knee spacer for temporary replacement of an artificial knee joint, the knee spacer comprising a tibial component and a femoral component, as separate components, which are movable with respect to each other in a patient-inserted state, wherein the tibial component and the femoral component each comprise at least one running surface, arranged on a running surface side of each of the tibial and femoral components, by means of which the tibial component and the femoral component are placable against each other such as to be mobile in the patient-inserted state, wherein the tibial component comprises an anchoring surface located on an anchoring surface side that is opposite with respect to the running surface side of the tibial component and provided for connecting the tibial component to the tibia by means of a bone cement, wherein the femoral component comprises an anchoring surface located on an anchoring surface side that is opposite with respect to the running surface side of the femoral component and provided for connecting the femoral component to the femur, wherein the tibial component and the femoral component each comprise at least two recesses extending from the anchoring surface located on the anchoring surface side of each of the tibial and femoral components into the running surface side of each of the tibial and femoral components, wherein first openings of the at least two recesses of the femoral component are arranged in the running surface side of the femoral component such that the first openings are not slidable over the running surface of the tibial component during articulation of the knee spacer and second openings of the at least two recesses of the tibial component are arranged in the running surface side of the tibial component such that the second openings are not slidable over the running surface of the femoral component during articulation of the knee spacer, wherein the femoral component has a total height defined between the anchoring surface side and the running surface side of the femoral component, a total length defined between a first end and a second end located opposite with respect to the first end of the femoral component and a total width defined between a first side and a second side located opposite with respect to the first side of the femoral component, wherein the first end of the femoral component comprises an end surface extending the total width of the femoral component from the first side of the femoral component to the second side of the femoral component, wherein the end surface of the first end of the femoral component comprises (i) first and second convex surfaces, (ii) the at least two recesses of the femoral component comprise concave surfaces, and (iii) at least one planar surface at a tip of the first end of the femoral component located, on the end surface of the femoral component, between the concave surfaces of the at least two recesses of the femoral component.

2. The knee spacer according to claim 1, wherein the at least two recesses of the tibial component are arranged on the periphery in the tibial component and the at least two recesses of the femoral component are arranged on the periphery in the femoral component.

3. The knee spacer according to claim 2, wherein at least two of the recesses of the femoral and tibial components are arranged opposite from each other such that, in the patient-inserted state of the femoral and tibial components, bone cement extensions formed in the at least two of the recesses of the femoral and tibial components clamp the femoral and tibial components such that regions of the femoral and tibial components are arranged between the bone cement extensions.

4. The knee spacer according to claim 1, wherein projections for anchoring the bone cement are arranged in the recesses.

5. The knee spacer according to claim 1, wherein at least one selected from the tibial component and the femoral component, in the inserted state, are at least one selected from (i) asymmetrical to a plane parallel to a sagittal plane of a patient, by means of at least one selected from an arrangement of a recess and shape of a recess for receiving the cruciate ligament of the patient and (ii) asymmetrical by means of at least one selected from an arrangement of the recesses and a shape of the recesses.

6. The knee spacer according to claim 1, wherein the recesses are designed as cylinders, truncated cones and/or multi-sided prisms, whereby at least one front side of the cylinders, truncated cones and/or prisms is open towards the anchoring surface and to the running surface side, and whereby the jacket surfaces of the cylinders, truncated cones and/or prisms are closed in longitudinal direction or are punctured once in axial direction.

7. The knee spacer according to claim 1, wherein at least one first guide element is arranged on the running surface side of the tibial component and at least one second guide element is arranged on the running surface side of the femoral component, whereby the at least one first and second guide elements, in the patient-inserted state, prevent the femoral component from shifting with respect to the tibial component in the direction of a plane parallel to a sagittal plane of a patient by means of a form-fit being established upon a rotary motion of the femoral and tibial components with respect to each other.

8. The knee spacer according to claim 1, wherein the tibial and femoral components are made up from at least one selected from at least one plastic material and metal.

9. The knee spacer according to claim 8, wherein the tibial and femoral components consist of at least one selected from a plastic material and metal.

10. The knee spacer according to claim 9, wherein the tibial and femoral components are made of antibiotics-doped cured polymethylmethacrylate bone cement.

11. The knee spacer according to claim 1, wherein the tibial component comprises a stem that extends from a central position of the anchoring surface at an angle of between 85° and 90° away from the anchoring surface, wherein the stem is provided for anchoring in a recess in the tibia and the stem extending away from the anchoring surface is convergent, at least over regions thereof.

12. The knee spacer according to claim 11, wherein the stem extends perpendicularly away from the anchoring surface.

13. The knee spacer according to claim 1, wherein multiple spacers are arranged on the anchoring surface of each of the femoral and tibial components, wherein the multiple spacers extending away from the anchoring surface are convergent, at least over regions thereof, and wherein the stem is at least four times as high as the spacers of the anchoring surface of the tibial component.

14. A method for manufacture of the knee spacer according to claim 1, the method comprising: producing the tibial component and the femoral component as separate components wherein at least two recesses are formed in the tibial component and at least two recesses are formed in the femoral component.

* * * * *